United States Patent
Vanek et al.

(10) Patent No.: US 9,746,409 B2
(45) Date of Patent: *Aug. 29, 2017

(54) METHOD AND APPARATUS FOR DETERMINING CLEANLINESS OF A SAMPLE

(71) Applicant: PERSYS TECHNOLOGY LTD., Kiryat Gat (IL)

(72) Inventors: Yitzhak Vanek, Los Gatos, CA (US); Leo Mendelovici, Mevaseret Ziyon (IL); Gideon Drimer, Herzeliya (IL)

(73) Assignee: PERSYS TECHNOLOGY LTD., Kiryat Gat (IL)

( * ) Notice: Subject to any disclaimer, the term of this patent is extended or adjusted under 35 U.S.C. 154(b) by 62 days.

This patent is subject to a terminal disclaimer.

(21) Appl. No.: 14/904,096

(22) PCT Filed: Jul. 11, 2013

(86) PCT No.: PCT/US2013/050148
§ 371 (c)(1),
(2) Date: Jan. 10, 2016

(87) PCT Pub. No.: WO2015/005929
PCT Pub. Date: Jan. 15, 2015

(65) Prior Publication Data
US 2016/0131567 A1    May 12, 2016

(51) Int. Cl.
*G01N 21/00* (2006.01)
*G01N 15/06* (2006.01)
*G01N 15/00* (2006.01)

(52) U.S. Cl.
CPC . *G01N 15/0612* (2013.01); *G01N 2015/0046* (2013.01)

(58) Field of Classification Search
CPC ............. G01N 21/53; G01N 15/0205; G01N 15/1459; G01N 21/51; G01N 15/1434
(Continued)

(56) References Cited

U.S. PATENT DOCUMENTS 5,895,869 A * 4/1999 Von Behrens ..... G01N 15/1404
73/865.5
5,914,454 A * 6/1999 Imbaro ............... B01D 53/1418
261/79.2
(Continued)

FOREIGN PATENT DOCUMENTS

JP    2006153709    6/2006
KR    100614101    8/2006

*Primary Examiner* — Tarifur Chowdhury
*Assistant Examiner* — Md M Rahman
(74) *Attorney, Agent, or Firm* — Daniel J. Swirsky; AlphaPatent Associates Ltd.

(57) ABSTRACT

A method and apparatus for determining cleanliness of a sample is provided. The method includes taking a first reading of particles count of a sample placed into a chamber. The method further includes directing a stream of air over the sample, and taking a second reading of particles count of the sample. The method further includes calculating a difference between the first reading and the second reading, and determining a cleanliness of the sample based upon the difference. The method further includes option of taking an additional reading while a stream of ionized air is directed towards the sample. The method further includes trapping the impurities particles released from the sample by applying a vacuum through the filter, and analyzing the trapped particles to determine nature and chemical composition of the impurities particles.

10 Claims, 6 Drawing Sheets

(58) Field of Classification Search
USPC .......................................................... 356/338
See application file for complete search history.

(56) References Cited

U.S. PATENT DOCUMENTS

| | | | |
|---|---|---|---|
| 6,327,021 B1 | 12/2001 | Higashiguchi | |
| 6,474,355 B1 | 11/2002 | Jirawat et al. | |
| 7,181,952 B2* | 2/2007 | Ditch | G01F 1/68 73/29.01 |
| 7,437,908 B2 | 10/2008 | Bae et al. | |
| 2007/0023694 A1 | 2/2007 | Kim et al. | |
| 2011/0068263 A1* | 3/2011 | Wouters | H01J 49/0445 250/282 |

* cited by examiner

METHOD AND APPARATUS FOR DETERMINING CLEANLINESS OF A SAMPLE

CROSS-REFERENCE TO RELATED APPLICATIONS

This application is a U.S. National Phase Application under 35 U.S.C. 371 of International Application No. PCT/US2013/050148, which has an international filing date of Jul. 11, 2013.

BACKGROUND

Field of the Invention

Embodiments of the present invention provide a method and apparatus for particle detection. More particularly, embodiments of the present invention provide a method and apparatus for determining cleanliness of a sample.

Description of Related Art

Contamination detection has become increasingly significant, particularly with rapid evolution of high-tech industries. For example, semiconductor industry has developed technology for precisely producing microelectronic devices and integrated circuits. In order to reliably produce such products, highly stringent contamination standards must be maintained in production facilities of such products.

In an effort to control contamination during a production process, clean rooms are frequently used. A clean room is a room in which air filtration, air distribution, utilities, materials of construction, equipment, and other operating procedures are specified and regulated to control airborne particle concentrations to meet appropriate airborne particulate cleanliness classifications. Clean rooms are used extensively in semiconductor manufacturing, biotechnology, pharmaceutical, disk drive, aerospace and other fields that are very sensitive to environmental contamination.

It is important to monitor and maintain the cleanliness/contamination levels in the clean rooms. Further, for maintaining the cleanliness/contamination levels in the clean room, it is important to test/inspect a sample for cleanliness standard, before sending the sample to the clean room. Hence, cleanliness of a new sample coming to the clean room environment is very important.

In addition, in the mentioned industries it is customary to carry out preventive maintenance of manufacturing tools such as sputtering, CVD, etch, and other tools. As part of this procedure some of the parts require renovation and cleaning. Therefore, it is of high importance to be able to test cleanliness of the part before reinstalling it to a machine.

Conventionally, visual inspection techniques have been used with ultraviolet or oblique white light. Ultraviolet light is employed to take advantage of the fact that certain organic particles fluoresce. Alternatively, white light is shined towards a test surface at an angle so as to produce reflections that can be visualized. While the white light technique is slightly more sensitive than the ultraviolet technique, they both suffer from a common limitation. These visual inspection techniques only allow a cursory inspection of the sample or surface conditions. Further, the visual inspection techniques, at best, only detect particles that are larger than twenty microns. If, it is desirable or requirement to detect particles that are less than one micron, conventional techniques fails to achieve the goal. Furthermore, these conventional techniques are very tedious and time consuming.

Other conventional techniques include particle counters, which are intended for measuring particles on the surface. However, one of the main disadvantages of this technique is that it is localized and does not account for the complete sample.

Yet another conventional technique include Liquid Particle Counters, which are intended for measuring particles removed from a sample after flowing clean water through the sample. However in this case the sample cannot be further used and needs to be either dissected or processed (cleaned) again.

Hence, there is a need for apparatus and method that can determine cleanliness of a sample, before shipping or taking the sample to clean room environment. Further, there is a need for a method and apparatus that can determine the cleanliness of the sample in a convenient and effective manner.

SUMMARY

Embodiments in accordance with the present invention provide a method for determining cleanliness of a sample. The method includes taking a reference reading of the empty chamber so a background or blank value is determined before introducing the sample into the chamber and while a constant flow of clean air from the HEPA filter-unit flows through the chamber constantly. The method further includes taking a first reading of particles count of a sample placed into a chamber. The next step includes directing a stream of air over the sample, and taking a second reading of particles count of the sample. The method further includes calculating a difference between the first reading and the second reading, and determining a cleanliness of the sample based upon the difference of the readings, taking into account the blank reading.

Embodiments in accordance with the present invention further provide an apparatus for determining cleanliness of a sample. The apparatus includes a HEPA filter unit with a blower, a chamber, a nozzle set, and a particle counter. The chamber includes a sample holder for holding a sample. The nozzle set is located in the chamber, and is configured to direct a stream of clean air into the sample. The stream of clean air is operated through a frictionless device such as a Venturi valve to avoid generation of particles. The particle counter is coupled with the chamber, and configured to count particles released from the sample.

Embodiments in accordance with the present invention further provide a method for determining cleanliness of a sample. The method includes taking a reference reading of the empty chamber as above, placing a sample into a chamber, and taking a first reading of particles count released from the sample. The method further includes directing a stream of ionized air over the sample, and taking a second reading of particles count released from the sample. The method further includes taking an additional reading while ESD is activated and calculating a difference between the readings to determine impurities particles count. The method further includes comparing the impurities particles count with a predetermined threshold value, and determining a cleanliness of the sample based upon the comparison.

Further, the present invention can provide a number of advantages depending on its particular configuration. First, embodiments of the present invention provide a system and a method for testing cleanliness of equipment parts and other samples, which can work in a clean room environment only after a cleanliness testing procedure has been carried out. Further, the present invention facilitates directly packing and shipping the samples, if they meet the cleanliness criteria. Hence, they may not require additional cleaning or drying procedures such as used in liquid particle counters (LPC), surface particle counters, or similar equipment.

Furthermore, the present invention utilizes a conventional particle counter for determining cleanliness of a sample. Hence, the present invention provides a convenient, simple, and effective method to determine cleanliness of the sample.

These and other advantages will be apparent from the disclosure of the present invention contained herein.

The preceding is a simplified summary of the present invention to provide an understanding of some aspects of the present invention. This summary is neither an extensive nor exhaustive overview of the present invention and its various embodiments. It is intended neither to identify key or critical elements of the present invention nor to delineate the scope of the present invention but to present selected concepts of the present invention in a simplified form as an introduction to the more detailed description presented below. As will be appreciated, other embodiments of the present invention are possible, utilizing alone or in combination, one or more of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings, and wherein.

Figure 1:
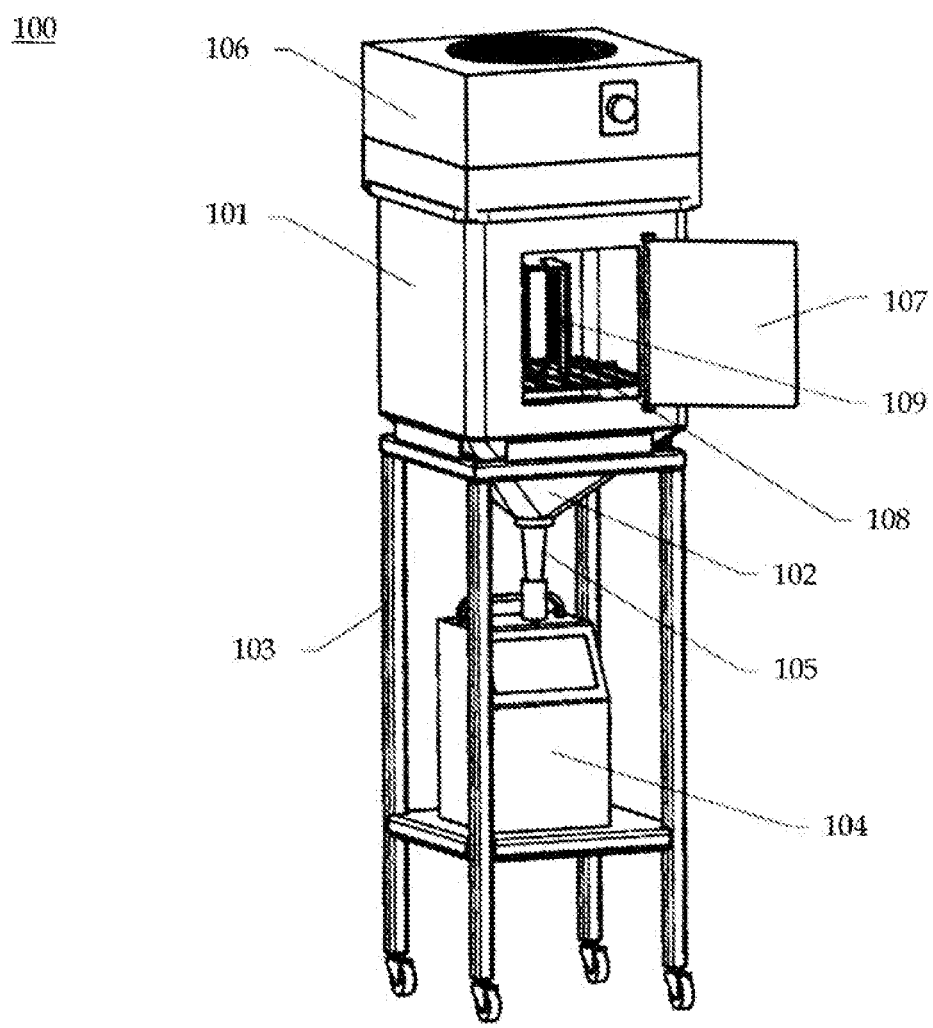
FIG. 1 shows a schematic diagram of front view of an apparatus, in accordance with an embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

DETAILED DESCRIPTION

The present invention will be illustrated below in conjunction with an exemplary method and apparatus for determining cleanliness of a sample. The present invention is not limited to any particular type of method and apparatus or configuration of system elements. Those skilled in the art will recognize the disclosed techniques may be used in any method or system in which it is desirable to determine cleanliness of a sample.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine", "calculate" and "compute," and variations thereof, as used herein, are used interchangeably and include any type of methodology, process, mathematical operation or technique.

Figure 2:
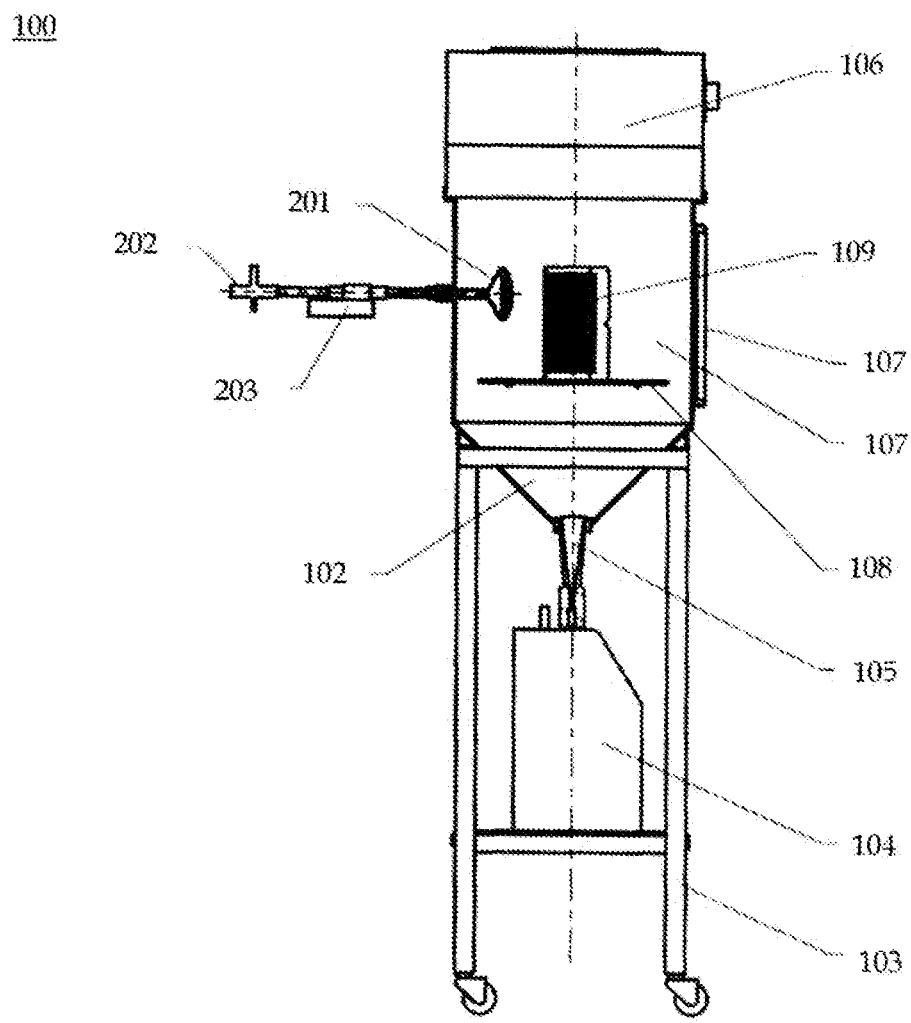
FIG. 2 shows a schematic diagram of side view of the apparatus according to an embodiment of the present invention.
Figure 3:
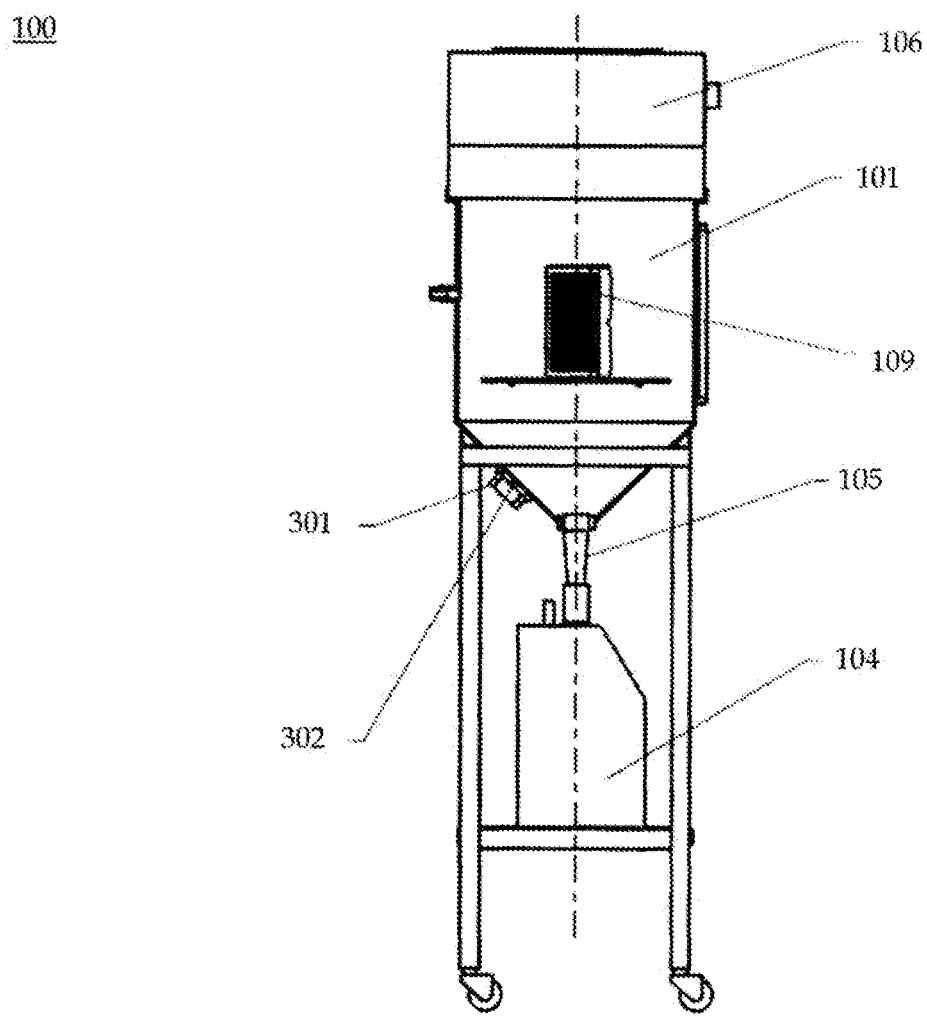
FIG. 3 shows another schematic diagram of side view of the apparatus according to an embodiment of the present invention.

FIGS. 1, 2, and 3 show schematic diagrams of front view and side view of an apparatus 100 respectively, in accordance with an embodiment of the present invention. The apparatus 100 includes a chamber 101 having a funnel shaped bottom section 102 supported by a stand 103. The chamber 101 is further coupled with a particle counter 104. In an embodiment of the present invention, the chamber 101 and the particle counter 104 may be connected through a counter iso-kinetic probe 105. In another embodiment, the chamber 101 and the particle counter 104 may be connected through any other suitable means.

Further, the apparatus 100 includes a HEPA filter 106 mounted with a blower. In an embodiment, the HEPA filter 106 may be a high efficiency (HEPA) filter 106. The HEPA filter 106 may be used for supplying a constant flow of clean air into the chamber 101 with the help of the blower. Furthermore, the apparatus 100 includes a door 107 that may be kept in an open position to access a sample holder 108 present within the apparatus. The sample holder 108 may be used to hold a sample 109 in position within the apparatus. In an embodiment, the sample holder 108 is designed to properly hold various types of samples.

In the present invention, sample relates to any machine part, tool, parts holders, wafers, disks, garments wipes, gloves etc that is used in a clean room environment.

In an embodiment, the particle counter 104 is configured to detect and count particles in the sample 109. Further, the particle counter 104 may be a single channel particle counter, and may detect and count particles of one particular size at a time. In another embodiment, the particle counter 104 may be able to count multiple particle sizes. Further, in an embodiment, the particle counter 104 may be a typical laser type particle counter or may operate based upon light scattering, light obscuration, or direct imaging.

Further, the sample 109 may include a metal part, quartz part, ceramic part, and plastic part, which may be used in a clean room environment for various applications, for example, machine parts, tools, gowns, gloves, clean room towels, etc. In an embodiment, the chamber 101 may be manufactured from various materials including metals, such as aluminum, stainless steel, glass (e.g., quartz, borosilicate glass, etc.), plastics etc. In another embodiment, the chamber 101 may be manufactured from any other convenient fabrication material or a combination of these materials.

The chamber 101 of the apparatus further includes a nozzle 201 (as shown in FIG. 2) for directing a stream of air into the sample. The stream of air may further include a frictionless device such as a pinch valve or a Venturi valve 202. The pinch valve or the Venturi valve 202 may be used for supplying a stream of clean air or ionized air. The apparatus 100 further includes an electrostatic discharge device (ESD) 203 (as shown in FIG. 2) for generating ionized air. The ESD device 203 is coupled with the nozzle 201. The apparatus 100 may further include a frictionless device (e.g., Venturi valve 202) for supplying stream of clean air or a stream of ionized clean air. The ESD device 203 is further needed to be activated in order to generate ionized air. In an embodiment of the present invention, air may constantly flow through the ESD device 203, and the ESD device 203 may be activated by supplying voltage.

In another embodiment of the present invention, voltage may be constantly applied on the ESD device 203 and the ionized air flow out of the clean chamber, through the Venturi valve 202 (as described above) in to the chamber 101 and over the sample 109. Once activated, the ESD device 203 may direct the ionized air over the sample. In an embodiment of the present invention, clean/ionized air constantly and continuously flows through the HEPA filter unit 106 into the chamber 101.

Further, in an embodiment of the present invention, the apparatus 100 may include a filter holder 301 holding a filter 302 (as shown in FIG. 3). The filter 302 is detachably located in the filter holder 301 and can be used for trapping particles released from the sample 109 upon applying a vacuum through the filter 302. The filter 302 can be further removed from the filter holder 301 and the nature and chemical composition of the particles can be further determined by conventional analytical methods.

Figure 4A:
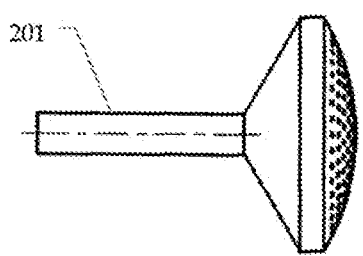
FIGS. 4A and 4B shows a typical set of nozzles for air injection.
Figure 4B:
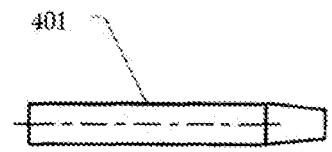

In an embodiment of the present invention, as shown in the FIGS. 4A and 4B of the present invention, the nozzle 201 may be in a shape of a shower head (as shown in FIG. 4A) or may be in a shape of a conventional nozzle (as shown in FIG. 4B). In another embodiment, the apparatus 100 may use a nozzle set having both the conventional nozzle and the shower head. In yet another embodiment, the nozzle 201 may be a nozzle set comprising a nozzle and/or a shower head. The nozzle set illustrated in FIGS. 4A and 4B are typically used for air injection.

Further, in an embodiment of the present invention, the apparatus 100 may further include an electronic control system (now shown in Figure) that may be used by an operator to operate the apparatus. In another embodiment, a programmable controller (not shown in Figure) may be used to operate the apparatus or system.

Furthermore, in an embodiment of the present invention, a personal computer (now shown in Figure) may be connected with the apparatus to control the operation of the system and acquire the readings of the particle counter 104, and further processing the readings to determine cleanliness of the sample 109 with appropriate software to control the system and acquire and process the readings.

Figure 5A:
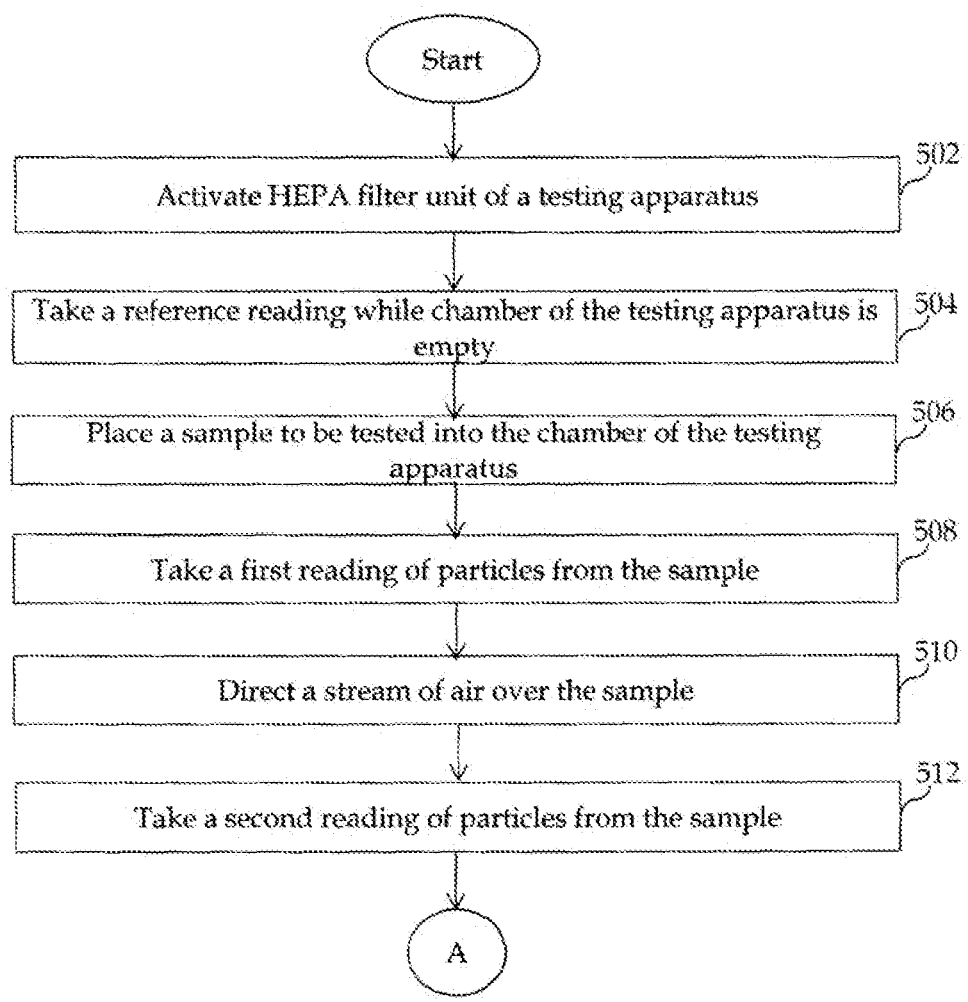
FIGS. 5A and 5B are a flowchart of a method for determining cleanliness of a sample, in accordance with an embodiment of the present invention.
Figure 5B:
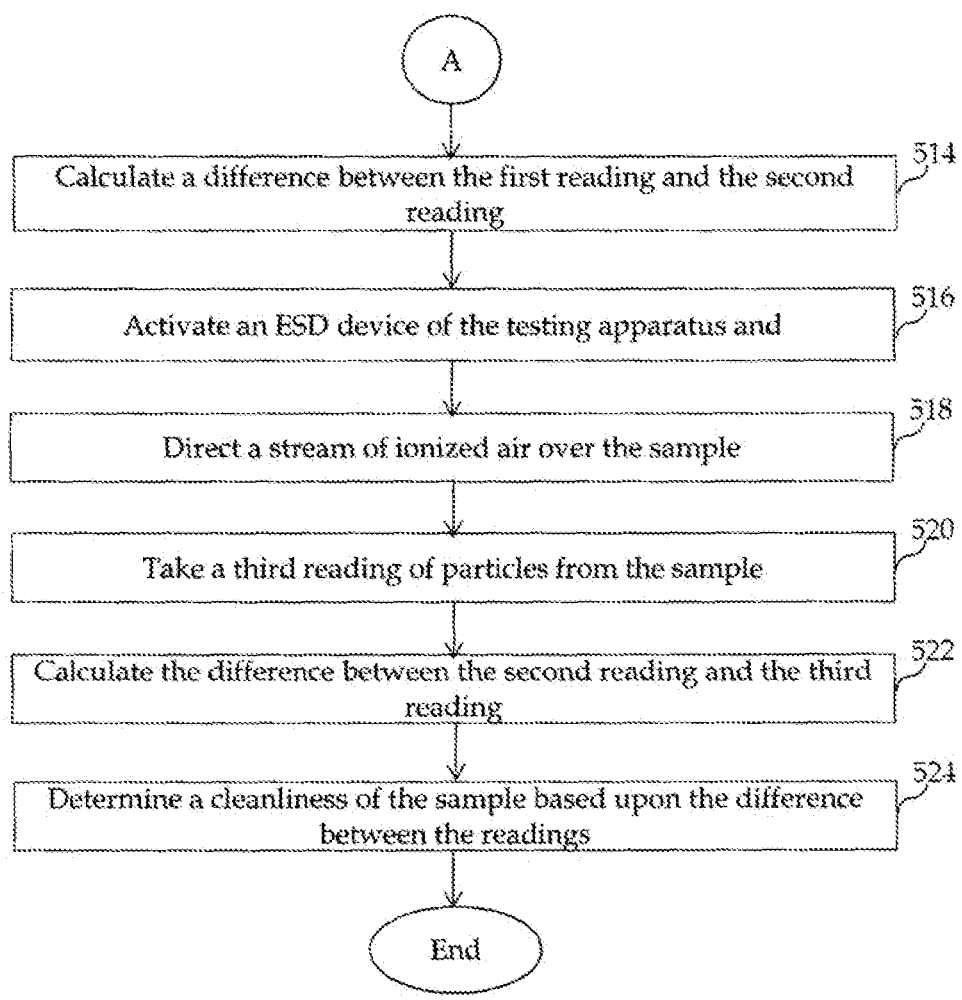

FIGS. 5A and 5B are a flowchart of a method 500 for determining cleanliness of a sample, in accordance with an embodiment of the present invention. A sample (such as, sample 109) is placed into a chamber (such as, chamber 101) of a testing apparatus (such as, testing apparatus 100, as shown in FIGS. 1, 2, and 3) that is designed to test cleanliness of various samples. In an embodiment of the present invention, the chamber 101 of the testing apparatus 100 may be manufactured from various materials including metals, such as aluminum, stainless steel, glass (e.g., quartz, borosilicate glass, etc.), plastics etc. In another embodiment, the chamber 101 may be manufactured from any other convenient fabrication material or a combination of these materials.

At step 502, HEPA filter unit 106 and a blower of the testing apparatus is activated. In an embodiment, the blower must be configured to blow a constant and continuous stream of clean air flow through the HEPA filter unit 106. Thereafter, at step 504, a reference reading is taken considering that the chamber 101 of the testing apparatus is empty. This reading may help in determining particles count within the apparatus before putting in a sample. In an embodiment, the reading may be taken by a particle counter (such as particle counter 104) of the testing apparatus.

At step 506, a sample to be tested for cleanliness (such as the sample 109) is placed into the chamber 101 of the testing apparatus 100. Specifically, the sample 109 may be placed into a sample holder (such as the sample holder 108), which is present inside the chamber 101 of the testing apparatus. The sample 109 may include a metal part, quartz part, ceramic part, and plastic part, which may be used in a clean room environment for various applications, for example, silicon wafers, magnetic disks, machine parts, gowns, gloves, clean room towels, etc. In an embodiment, the sample holder 108 is designed to properly hold various types of samples.

At step 508, a first reading of particles count of the sample 109 (present inside the apparatus) is taken with the particle counter 104. The first reading of particles count of the sample 109 may represent the fraction of loose particles present in the sample. Thereafter, at step 510, a stream of clean air is directed over the sample 109. In an embodiment, a stream of ionized air may also be directed over the sample 109. An ESD device (such as ESD device 203) may be used to generate the ionized air. Further, the stream of air directed over the sample may release some additional contamination or impurities particles present (if present) on the sample 109.

At step 512, a second reading (after directing stream of air over the sample) of particles count released from the sample 109 is taken with the particle counter 104. The particles count noticed from the second reading may represent particles remaining in the sample 109 after release of some contamination/particles by directing a stream of clean air over the sample 109. In an embodiment, the readings of the particle count are taken as a function of time or after pre-determined time interval. Further, at step 514 (as shown in FIG. 5B), a difference between the first reading and the second reading is calculated. In an embodiment, the difference may determine contamination/impurities particles count released from the sample due to strike by the stream of air.

At step 516, the ESD device 203 is activated and at step 518 a stream of clean ionized air is directed over the sample. Thereafter, at step 520 an additional reading (third reading) of the particle count from the sample 109 is taken with the particle counter 104 (while the ESD device 203 is active). Then, at step 522, a difference between the second reading and the third reading is calculated. In an embodiment, the difference may determine contamination/impurities particles count released from the sample due to strike by the stream of clean ionized air At step 524, cleanliness of the sample 109 is determined based upon the difference between the measured readings. In an embodiment, the difference (i.e., contamination/impurities particle count) may be compared with a predetermined threshold value, and the cleanliness of the sample 109 may be determined based upon the comparison. For example, if the difference is less than the predetermined threshold value, the sample may be determined to be in a clean state. Otherwise, the sample may be determined to be in an unclean state. The predetermined threshold value may be set based upon cleanliness standard required in production facility or clean room. In an embodiment, the reference reading taken in the step 504 may be considered to determine a threshold value.

Furthermore, the description above is meant for illustration purposes only and different methodology can be used to determine the cleanliness of a sample. For example continuous readings of the particle counter can be recorded after placing the sample into the chamber, directing a stream of air over the sample, directing a stream of ionized air over the sample, etc. For the values recorded a graph or table can be generated and the influence of each step can be determined in addition to the cleanliness of the sample.

Further, in an optional step (not shown in figure), the contamination/impurities particles released from the sample air may be trapped by a filter 302 by applying a vacuum through the filter holder 301 and filter 302. The trapped particles may be further analyzed to determine nature and chemical composition of the impurities particles.

According to an embodiment of the present invention, the contamination/impurities particle may be present over surface of the sample 109. If number of contamination/impurities particles (i.e., the difference between the readings) released due to strike by the stream of clean air, or and the strike of ionized clean air generated by the ESD 203 is more than the predetermined threshold, the sample 109 may have too many contamination/impurities particle present over it, that it is not fit to be taken to a clean room or production facility. Hence, the sample 109 may be cleaned, and then the sample 109 may be again tested for cleanliness criteria. This process may be repeated till the cleanliness of the sample 109 is within cleanliness standard required in the production facility/clean room.

In an embodiment of the present invention, the reading data may be automatically acquired by a computer (not shown in the figures) attached to the apparatus and further processed to determine cleanliness of the sample 109. The computer may have appropriate software installed (in addition to display, memory, and processor), that may acquire the readings taken, process the readings, and automatically determine cleanliness of the sample 109.

In another embodiment of the present invention, the functionality as well as the readings from the particle counter can be controlled by a Logic Programmable Controller (LPC) (not shown in the figures) that includes a graphic display unit to interact with the operator. Moreover, the LPC can be connected to a computer with appropriate software to store, process and evaluate the results.

In another embodiment of the present invention, the reading data may be manually read and processed by an operator (i.e., the difference between the readings may be manually carried by an operator) of the apparatus to determine cleanliness of the sample 109.

Also, while the flowcharts have been discussed and illustrated in relation to a particular sequence of events, it should be appreciated that changes, additions, and omissions to this sequence can occur without materially affecting the operation of the present invention.

A number of variations and modifications of the present invention can be used. It would be possible to provide for some features of the present invention without providing others.

The present invention, in various embodiments, configurations, and aspects, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the present invention has been presented for purposes of illustration and description. The foregoing is not intended to limit the present invention to the form or forms disclosed herein. In the foregoing Detailed Description for example, various features of the present invention are grouped together in one or more embodiments, configurations, or aspects for the purpose of streamlining the disclosure. The features of the embodiments, configurations, or aspects of the present invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the present invention.

Moreover, though the description of the present invention has included description of one or more embodiments, configurations, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for determining cleanliness of a sample, the method comprising:
   an operating apparatus,
   wherein said operating apparatus comprising:
   a chamber having a funnel shaped bottom section and a sample holder for holding a sample in said chamber,
   a HEPA filter unit with a blower disposed above said chamber and in fluid connection with said chamber; said blower adapted to provide a constant flow of clean air to said chamber,
   a valve coupled to a nozzle set and an electrostatic discharge device (ESD) for generating ionized air, located in said chamber, said nozzle set configured to direct a stream of clean air onto the sample, and a particle counter, coupled with the chamber via a counter iso-kinetic probe:

wherein the operating apparatus determines the cleanliness of the sample by the following steps:
- a) providing a continuous flow of clean air into the chamber,
- b) taking a reference reading of a particle count while said chamber is empty,
- c) introducing said sample into the chamber,
- d) taking a first reading of a particle count received from all sides of said sample in said chamber to determine loose particles associated with said sample,
- e) directing a stream of at least one of clean air and ionized air over said sample,
- f) taking a second reading of particles count of said sample, and
- g) calculating a difference between the first reading and the second reading thereby determining said cleanliness of said sample based upon said difference.

2. The method of claim 1, wherein a third reading is taken during said directing step and wherein said cleanliness of said sample is calculated based upon difference between the third reading and the second reading, or between the three readings, while taking into account said reference reading.

3. The method of claim 1, wherein the determining comprises comparing the difference with a predetermined threshold.

4. The method of claim 1, wherein the difference represents an impurities particles count.

5. The method of claim 4, further comprising trapping the impurities particles released from the sample due to said stream of at least one of said clean and said ionized air.

6. The method of claim 5, further comprising analyzing the trapped particles to determine nature and chemical composition of the impurities particles.

7. The method of claim 1, wherein the sample is selected from at least one of a metal part, quartz part, ceramic part, and plastic part.

8. The method of claim 1, wherein the sample is selected from at least one of a machine part, a tool, a clean room gown, a clean room glove and a clean room towel.

9. A method for determining cleanliness of a sample, the method comprising:

an operating apparatus, wherein said operating apparatus comprising:
- a chamber having a funnel shaped bottom section and a sample holder for holding a sample in said chamber,
- a HEPA filter unit with a blower disposed above said chamber and in fluid connection with said chamber; said blower adapted to provide a constant flow of clean air to said chamber,
- a valve coupled to a nozzle set and an electrostatic discharge device (ESD) for generating ionized air, located in said chamber, said nozzle set configured to direct a stream of clean air onto the sample, and
- a particle counter, coupled with the chamber via a counter iso-kinetic probe :

wherein the operating apparatus determines the cleanliness of the sample by the following steps:

placing a sample into the chamber, taking a first reading of particles count of the sample, directing a stream at least one of clean air of ionized air over the sample, taking a second reading of particles count of the sample, taking an additional reading while an electrostatic device (ESD) is activated, calculating a difference between the readings to determine impurities particles count, comparing the impurities particles count with a predetermined threshold value, and determining a cleanliness of the sample based upon the comparison.

10. The method of claim 9, further comprising analyzing the trapped particles to determine nature and chemical composition of the impurities particles.

* * * * *